(12) United States Patent
Meissner et al.

(10) Patent No.: US 7,109,191 B2
(45) Date of Patent: Sep. 19, 2006

(54) BENZAZEPINONE ALPHA VINTEGRIN RECEPTOR ANTAGONISTS

(75) Inventors: Robert S. Meissner, Schwenksville, PA (US); Paul J. Coleman, Wallingford, PA (US); Mark E. Duggan, Harleysville, PA (US); George D. Hartman, Lansdale, PA (US); Jiabing Wang, Chalfont, PA (US); John H. Hutchinson, La Jolla, CA (US)

(73) Assignee: Merck & Co., Inc., Rahway, NJ (US)

( * ) Notice: Subject to any disclaimer, the term of this patent is extended or adjusted under 35 U.S.C. 154(b) by 150 days.

(21) Appl. No.: 10/475,697

(22) PCT Filed: Apr. 29, 2002

(86) PCT No.: PCT/US02/13457

§ 371 (c)(1),
(2), (4) Date: Oct. 21, 2003

(87) PCT Pub. No.: WO02/090325

PCT Pub. Date: Nov. 14, 2002

(65) Prior Publication Data

US 2004/0142919 A1    Jul. 22, 2004

Related U.S. Application Data

(60) Provisional application No. 60/288,578, filed on May 3, 2001.

(51) Int. Cl.
*C07D 401/02* (2006.01)
*A61K 31/55* (2006.01)
*A61P 19/10* (2006.01)

(52) U.S. Cl. .................................. 514/212.07; 540/523

(58) Field of Classification Search ................ 540/523; 514/212.07
See application file for complete search history.

(56) References Cited

U.S. PATENT DOCUMENTS 6,232,308 B1    5/2001   Askew
6,825,188 B1 *  11/2004  Callahan et al. ....... 514/212.07

FOREIGN PATENT DOCUMENTS

| WO | WO 98/14192 | 4/1998 |
| WO | WO 00/46215 | 8/2000 |
| WO | WO 00/48603 | 8/2000 |

* cited by examiner

*Primary Examiner*—Bruck Kifle
(74) *Attorney, Agent, or Firm*—Patricia A. Shatynski; Mark R. Daniel

(57) ABSTRACT

The present invention relates to novel benzazepinone derivatives, their synthesis, and their use as αv integrin receptor antagonists. More particularly, the compounds of the present invention are antagonists of the integrin receptors αvβ3 and αvβ5 and are therefore useful for inhibiting bone resorption, treating and/or preventing osteoporosis, and inhibiting vascular restenosis, diabetic retinopathy, macular degeneration, angiogenesis, atherosclerosis, inflammatory arthritis, cancer, and metastatic tumor growth.

9 Claims, No Drawings

BENZAZEPINONE ALPHA VINTEGRIN RECEPTOR ANTAGONISTS

This aplication claims the benefit of U.S. Provisional Application No. 60/288,578, filed May 3, 2001.

FIELD OF THE INVENTION

The present invention relates to benzazepinone derivatives, their synthesis, and their use as αv integrin receptor antagonists. More particularly, the compounds of the present invention are antagonists of the integrin receptors αvβ3, αvβ5, and αv integrin receptors associated with other β-subunits, and are useful for inhibiting bone resorption, treating and/or preventing osteoporosis, and inhibiting vascular restenosis, diabetic retinopathy, macular degeneration, angiogenesis, atherosclerosis, inflammatory arthritis, cancer, and metastatic tumor growth.

BACKGROUND OF THE INVENTION

It is believed that a wide variety of disease states and conditions can be mediated by acting on integrin receptors and that integrin receptor antagonists represent a useful class of drugs. Integrin receptors are heterodimeric transmembrane receptors through which cells attach and communicate with extracellular matrices and other cells. (See S. B. Rodan and G. A. Rodan, "Integrin Function In Osteoclasts," *Journal of Endocrinology*, 154: S47–S56 (1997), which is incorporated by reference herein in its entirety).

In one aspect of the present invention, the compounds disclosed herein are useful for inhibiting bone resorption. Bone resorption is mediated by the action of cells known as osteoclasts. Osteoclasts are large multinucleated cells of up to about 400 mm in diameter that resorb mineralized tissue, chiefly calcium carbonate and calcium phosphate, in vertebrates. Osteoclasts are actively motile cells that migrate along the surface of bone, and can bind to bone, secrete necessary acids and proteases, thereby causing the actual resorption of mineralized tissue from the bone. More specifically, osteoclasts are believed to exist in at least two physiological states, namely, the secretory state and the migratory or motile state. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone.

Integrins are involved in osteoclast attachment, activation and migration. The most abundant integrin on osteoclasts, e.g., on rat, chicken, mouse and human osteoclasts, is an integrin receptor known as αvβ3, which is thought to interact in bone with matrix proteins that contain the RGD sequence. Antibodies to αvβ3 block bone resorption in vitro indicating that this integrin plays a key role in the resorptive process. There is increasing evidence to suggest that αvβ3 ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, αvβ3 ligands have been found to be useful in treating and/or inhibiting restenosis (i.e. recurrence of stenosis after corrective surgery on the heart valve), atherosclerosis, diabetic retinopathy, macular degeneration, and angiogenesis (i.e. formation of new blood vessels), and inhibiting viral disease. Moreover, it has been postulated that the growth of tumors depends on an adequate blood supply, which in turn is dependent on the growth of new vessels into the tumor; thus, inhibition of angiogenesis can cause tumor regression in animal models (See *Harrison's Principles of Internal Medicine*, 12th ed., 1991, which is incorporated by reference herein in its entirety). Therefore, αvβ3 antagonists which inhibit angiogenesis can be useful in the treatment of cancer by inhibiting tumor growth (See, e.g., Brooks et al., *Cell*, 79:1157–1164 (1994), which is incorporated by reference herein in its entirety).

Evidence has also been presented suggesting that angiogenesis is a central factor in the initiation and persistence of arthritic disease, and that the vascular integrin αvβ3 may be a preferred target in inflammatory arthritis. Therefore, αvβ3 antagonists which inhibit angiogenesis may represent a novel therapeutic approach to the treatment of arthritic disease, such as rheumatoid arthritis (see C. M. Storgard, et al., "Decreased angiogenesis and arthritic disease in rabbits treated with an αvβ3 antagonist," *J. Clin. Invest.*, 103: 47–54 (1999); "Cilengitide," *Drugs of the Future*, 25: 674–678 (2000); and A. M. Badger, et al., "Disease-Modifying Activity of SB 273005, An Orally Active, Nonpeptide αvβ3 (Vitronectin Receptor) Antagonist, in Rat Adjuvant-Induced Arthritis," *Arthritis & Rheumatism*, 44: 128–137 (2001); each of which is incorporated by reference herein in its entirety).

Moreover, the compounds of this invention can also inhibit neovascularization by acting as an antagonist of the integrin receptor αvβ5. A monoclonal antibody for αvβ5 has been shown to inhibit VEGF-induced angiogenesis in rabbit cornea and the chick chorioallantoic membrane model (See M. C. Friedlander, et al., *Science* 270: 1500–1502 (1995), which is incorporated by reference herein in its entirety). Thus, compounds that antagonize αvβ5 are useful for treating and preventing macular degeneration, diabetic retinopathy, cancer, and metastatic tumor growth.

Additionally, the compounds of the instant invention can inhibit angiogenesis and inflammation by acting as antagonists of αv integrin receptors associated with other β subunits, suh as αvβ6 and αvβ8 (See, for example, Melpo Christofidou-Solomidou, et al., "Expression and Function of Endothelial Cell αv Integrin Receptors in Wound-Induced Human Angiogenesis in Human Skin/SCID Mice Chimeras," *American Journal of Pathology*, 151: 975–83 (1997) and Xiao-Zhu Huang, et al., "Inactivation of the Integrin β6 Subunit Gene Reveals a Role of Epithelial Integrins in Regulating Inflammation in the Lungs and Skin," *Journal of Cell Biology*, 133: 921–28 (1996), which are incorporated by reference herein in their entirety).

In addition, the compounds of this invention can also antagonize both the αvβ3 and αvβ5 receptors and is therefore useful for inhibiting bone resorption, treating and preventing osteoporosis, and inhibiting vascular restenosis, diabetic retinopathy, macular degeneration, angiogenesis, atherosclerosis, inflammatory arthritis, cancer, and metastatic tumor growth.

Peptidyl as well as peptidomimetic antagonists of the αvβ3 integrin receptor have been described both in the scientific and patent literature. For example, reference is made to W. J. Hoekstra and B. L. Poulter, *Curr. Med. Chem.* 5: 195–204 (1998) and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; WO 00/03973; EP 853084; EP 854140; EP 854145; U.S. Pat. Nos. 5,204,350; 5,217,994; 5,639,754; 5,741,796; 5,780,426; 5,929,120; 5,952,341; 6,017,925; and 6,048,861. Evidence of the ability of αvβ3 integrin receptor antagonists to prevent bone resorption in vitro and in vivo has been presented (see V. W. Engleman et al., "A Peptidomimetic Antagonist of the αvβ3 Integrin Inhibits Bone Resorption In Vitro and Prevents Osteoporosis In Vivo," *J. Clin. Invest.* 99: 2284–2292 (1997); S. B. Rodan et al., "A High Affinity Non-Peptide αvβ3 Ligand Inhibits Osteoclast Activity In Vitro and In Vivo," *J. Bone Miner. Res.* 11: S289 (1996); J. F. Gourvest et al., "Prevention of OVX-Induced Bone Loss With a Non-peptidic Ligand of the αvβ3 Vitronectin Receptor," *Bone* 23: S612 (1998); M. W. Lark et al., "An Orally Active Vitronectin Receptor αvβ3 Antagonist Prevents Bone Resorption In Vitro and In Vivo in the Ovariectomized Rat," *Bone* 23: S219 (1998)).

The αvβ3 integrin receptor recognizes the Arg-Gly-Asp (RGD) tripeptide sequence in its cognate matrix and cell surface glycoproteins (see J. Samanen, et al., "Vascular Indications for Integrin αv Antagonists," *Curr. Pharmaceut. Design* 3: 545–584 (1997)). A benzazepine nucleus has been employed among others by Genentech and SmithKline Beecham as a conformationally constrained Gly-Asp mimetic to elaborate nonpeptide αvβ3 integrin receptor antagonists substituted at the N-terminus with heterocyclic arginine mimetics (see R. M. Keenan et al., "Discovery of Potent Nonpeptide Vitronectin Receptor (αvβ3) Antagonists," *J. Med. Chem.* 40: 2289–2292 (1997); R. M. Keenan et al., "Benzimidazole Derivatives As Arginine Mimetics in 1,4-Benzodiazepine Nonpeptide Vitronectin Receptor (αvβ3) Antagonists," *Bioorg. Med. Chem. Lett.* 8: 3165–3170 (1998); and R. M. Keenan et al., "Discovery of an Imidazopyridine-Containing 1,4-Benzodiazepine Nonpeptide Vitronectin Receptor (αvβ3) Antagonist With Efficacy in a Restenosis Model," *Bioorg. Med. Chem. Lett.* 8: 3171–3176 (1998). Patents assigned to SmithKline Beecham that disclose such benzazepine, as well as related benzodiazepine and benzocycloheptene, αvβ3 integrin receptor antagonists include WO 96/00574, WO 96/00730, WO 96/06087, WO 96/26190, WO 97/24119, WO 97/24122, WO 97/24124, WO 98/14192, WO 98/15278, WO 99/05107, WO 99/06049, WO 99/15170, WO 99/15178, WO 99/15506, and U.S. Pat. No. 6,159,964, and to Genentech include WO 97/34865. The dibenzocycloheptene, dibenzocycloheptane and dibenzoxazepine scaffolds have also been employed as a Gly-Asp mimetic to afford αvβ3 antagonists (see WO 97/01540, WO 98/30542, WO 99/11626, WO 99/15508, WO 00/33838, U.S. Pat. Nos. 6,008,213, and 6,069,158, all assigned to SmithKline Beecham).

Other integrin receptor antagonists incorporating backbone conformational ring constraints have been described in the patent literature. Published patent applications or issued patents disclosing antagonists having a phenyl constraint include WO 98/00395, WO 99/32457, WO 99/37621, WO 99/44994, WO 99/45927, WO 99/52872, WO 99/52879, WO 99/52896, WO 00/06169, EP 0 820,988, EP 0 820,991, U.S. Pat. Nos. 5,741,796; 5,773,644; 5,773,646; 5,843,906; 5,852,210; 5,929,120; 5,952,381; 6,028,223; and 6,040,311. Published patent applications or issued patents disclosing antagonists having a monocyclic ring constraint include WO 99/26945, WO 99/30709, WO 99/30713, WO 99/31099, WO 99/59992, WO 00/00486, WO 00/09503, EP 0 796,855, EP 0 928,790, EP 0 928,793, U.S. Pat. Nos. 5,710,159; 5,723,480; 5,981,546; 6,017,926; and 6,066,648. Published patent applications or issued patents disclosing antagonists having a bicyclic ring constraint include WO 98/23608, WO 98/35949, WO 99/33798, EP 0 853,084, U.S. Pat. Nos. 5,760,028; 5,919,792; and 5,925,655.

Reference is also made to the following reviews for additional scientific and patent literature that concern alpha v integrin antagonists: M. E. Duggan, et al., "Ligands to the integrin receptor $\alpha_v\beta_3$, *Exp. Opin. Ther. Patents*, 10: 1367–1383 (2000); M. Gowen, et al., "Emerging therapies for osteoporosis," *Emerging Drugs*, 5: 1–43 (2000); J. S. Kerr, et al., "Small molecule $\alpha_v$ integrin antagonists: novel anticancer agents," *Exp. Opin. Invest. Drugs*, 9: 1271–1291 (2000); and W. H. Miller, et al., "Identification and in vivo efficacy of small-molecule antagonists of integrin $\alpha_v\beta_3$ (the vitronectin receptor)," *Drug Discovery Today*, 5: 397–408 (2000).

However, there still remains a need for small-molecule, non-peptidic selective αv integrin receptor antagonists that display improved potency, pharmacodynamic, and pharmacokinetic properties, such as oral bioavailability and duration of action, over already described compounds. Such compounds would provide an enhancement in the treatment, prevention, or suppression of various pathologies enumerated above that are mediated by αv integrin receptor binding and cell adhesion and activation.

In WO 00/48603 (Aug. 24, 2000) and WO 00/46215 (Aug. 10, 2000), we disclosed a series of dibenzazepine and benzazepine derivatives, respectively, which are αv integrin receptor antagonists. In the present invention, we describe novel benzazepinone derivatives with potent αv integrin receptor antagonistic properties.

It is therefore an object of the present invention to provide novel benzazepinone derivatives, which are useful as αv integrin receptor antagonists.

It is another object of the present invention to provide novel benzazepinone derivatives which are useful as αvβ3 receptor antagonists.

It is another object of the present invention to provide novel benzazepinone derivatives which are useful as αvβ5 receptor antagonists.

It is another object of the present invention to provide novel benzazepinone derivatives which are useful as dual αvβ3/αvβ5 receptor antagonists.

It is another object of the present invention to provide pharmaceutical compositions comprising the αv integrin receptor antagonists.

It is another object of the present invention to provide methods for making the pharmaceutical compositions of the present invention.

It is another object of the present invention to provide methods for eliciting an αv integrin receptor antagonizing effect in a mammal in need thereof by administering the compounds and pharmaceutical compositions containing the compounds of the present invention.

It is another object of the present invention to provide compounds and pharmaceutical compositions containing the compounds useful for inhibiting bone resorption, restenosis, atherosclerosis, inflammatory arthritis, diabetic retinopathy, macular degeneration, angiogenesis, cancer, and metastatic tumor growth.

It is another object of the present invention to provide compounds and pharmaceutical compositions containing the compounds useful for treating osteoporosis.

It is another object of the present invention to provide methods for inhibiting bone resorption, restenosis, atherosclerosis, inflammatory arthritis, diabetic retinopathy, macular degeneration, angiogenesis, cancer, and metastatic tumor growth.

It is another object of the present invention to provide methods for treating osteoporosis.

These and other objects will become readily apparent from the detailed description which follows.

SUMMARY OF THE INVENTION

The present invention relates to compounds of structural formula I:

(I)

or a pharmaceutically acceptable salt or ester thereof.

The present invention also relates to pharmaceutical compositions comprising the compounds of the present invention and a pharmaceutically acceptable carrier.

The present invention also relates to methods for making the pharmaceutical compositions containing the compounds of the present invention.

The present invention also relates to methods for eliciting an αv integrin receptor antagonizing effect in a mammal in need thereof by administering the compounds and pharmaceutical compositions containing the compounds of the present invention.

The present invention also relates to methods for inhibiting bone resorption, restenosis, atherosclerosis, inflammatory arthritis, diabetic retinopathy, macular degeneration, angiogenesis, cancer, and metastatic tumor growth by administering the compounds and pharmaceutical compositions containing the compound of the present invention.

The present invention also relates to methods for treating osteoporosis by administering the compounds and pharmaceutical compositions containing the compounds of the present invention.

DETAILED DESCRIPTION OF THE INVENTION

The present invention comprises compounds of structural formula I:

(I)

or a pharmaceutically acceptable salt thereof;

wherein X is selected from the group consisting of wherein the aromatic ring carbon atoms are unsubstituted or substituted with one $R^2$ substituent and the non-aromatic ring carbon atoms are unsubstituted or substituted with one or two $R^2$ substituents;

$R^2$ is selected from the group consisting of hydrogen, $C_{1-4}$ alkyl, and $C_{3-6}$ cycloalkyl; or two $R^2$ substituents, when on the same non-aromatic carbon atom, are taken together with the carbon atom to which they are attached to form a cyclopropyl group;

$R^1$ is hydrogen or $C_{1-4}$ alkyl; and $R^3$ and $R^4$ are each independently hydrogen or $C_{1-4}$ alkyl.

In certain embodiments of the present invention, the compounds correspond to the formula II with the designated (S)-stereochemistry at the stereogenic carbon atom marked with an asterisk:

(II)

wherein the substituents X, $R^1$, $R^2$, $R^3$, and $R^4$ are as described above.

Illustrative but nonlimiting examples of compounds of the present invention that are useful as αv integrin receptor antagonists are the following:

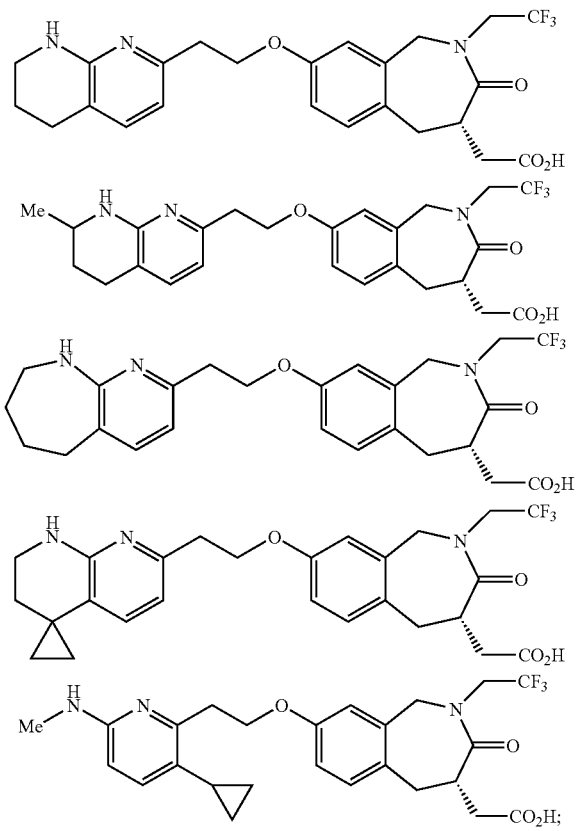

or a pharmaceutically acceptable salt thereof.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts of basic compounds encompassed within the term "pharmaceutically acceptable salts" refer to non-toxic salts of the compound of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carries an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, 2-methyl-2-amino-1-propanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The compounds of the present invention can have chiral centers and can thus occur as racemates, racemic mixtures, single enantiomers, diastereomeric mixtures, and individual diastereomers, with all isomeric forms being included in the present invention. Therefore, where a compound is chiral, the separate enantiomers or diastereomers, substantially free of the other, are included within the scope of the invention; further included are all mixtures of the two enantiomers.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form, known as keto-enol tautomers. The individual tautomers as well as mixtures thereof are encompassed within the compounds of the present invention.

Compounds of the present invention may be separated into diastereoisomeric pairs of enantiomers by, for example, fractional crystallization from a suitable solvent, for example, methanol or ethyl acetate or a mixture thereof. The pair of enantiomers thus obtained may be separated into individual stereoisomers by conventional means, for example, by the use of an optically active acid as a resolving agent, or by HPLC using a chiral stationary phase. Alternatively, any enantiomer of a compound of the present invention may be obtained by stereospecific synthesis using optically pure starting materials or reagents of known configuration.

Also included within the scope of the invention are polymorphs and solvates, such as hydrates, of the compounds of the instant invention.

The present invention includes within its scope prodrugs of the compounds of this invention. In general, such prodrugs will be functional derivatives of the compounds of this invention which are readily convertible in vivo into the required compounds. Thus, in the methods of treatment of the present invention, the term "administering" shall encompass the treatment of the various conditions described with the compounds specifically disclosed or with compounds which may not be specifically disclosed, but which convert to the specified compounds in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of the compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "αv integrin receptor antagonist," as used herein, refers to a compound which binds to and antagonizes either the αvβ3 receptor or the αvβ5 receptor, or a compound which binds to and antagonizes a combination of these receptors (for example, a dual αvβ3/αvβ5 receptor antagonist).

The term "bone resorption," as used herein, refers to the process by which osteoclasts degrade bone.

The compounds of the present invention displays submicromolar affinity for the αv integrin receptors, particularly the αvβ3 and αvβ5 receptors. The compounds of this invention are therefore useful for treating mammals suffering from a bone condition caused or mediated by increased bone resorption, who are in need of such therapy. Pharmacologically effective amounts of the compound, including pharmaceutically acceptable salts thereof, are administered to the mammal, to inhibit the activity of mammalian osteoclasts.

The compounds of the present invention are administered in dosages effective to antagonize the αvβ3 receptor where such treatment is needed, as, for example, in the prevention or treatment of osteoporosis.

Illustrating the invention is the method wherein the αv integrin receptor antagonizing effect is an αvβ3 antagonizing effect. More particularly, the αvβ3 antagonizing effect is selected from inhibition of: bone resorption, restenosis, angiogenesis, diabetic retinopathy, macular degeneration, inflammatory arthritis, cancer, and metastatic tumor growth. In one embodiment of the method, the αvβ3 antagonizing effect is the inhibition of bone resorption.

Another example of the invention is the method wherein the αv integrin receptor antagonizing effect is an αvβ5 antagonizing effect. More specifically, the αvβ5 antagonizing effect is selected from inhibition of restenosis, angiogenesis, diabetic retinopathy, macular degeneration, inflammatory arthritis, cancer, and metastatic tumor growth.

Further illustrating the invention is the method wherein the αv integrin receptor antagonizing effect is a dual αvβ3/αvβ5 antagonizing effect. More particularly, the dual αvβ3/αvβ5 antagonizing effect is selected from inhibition of: bone resorption, restenosis, angiogenesis, diabetic retinopathy, macular degeneration, inflammatory arthritis, cancer, and metastatic tumor growth.

More particularly illustrating the invention is a pharmaceutical composition comprising the compounds of the present invention and a pharmaceutically acceptable carrier. Another example of the invention is a pharmaceutical composition made by combining the compounds described above and a pharmaceutically acceptable carrier. Another illustration of the invention is a process for making a pharmaceutical composition comprising combining the compounds described above and a pharmaceutically acceptable carrier.

Further illustrating the invention is a method of treating and/or preventing a condition mediated by antagonism of an αv integrin receptor in a mammal in need thereof, comprising administering to the mammal a therapeutically effective amount of the compounds described above. Preferably, the condition is selected from bone resorption, osteoporosis, restenosis, diabetic retinopathy, macular degeneration, angiogenesis, atherosclerosis, inflammatory arthritis, cancer, tumor growth, and metastasis. More preferably, the condition is selected from osteoporosis and cancer. Most preferably, the condition is osteoporosis.

More specifically exemplifying the invention is a method of eliciting an αv integrin antagonizing effect in a mammal in need thereof, comprising administering to the mammal a therapeutically effective amount of the compounds or any of the pharmaceutical compositions described above. Preferably, the αv integrin antagonizing effect is an αvβ3 antagonizing effect; more specifically, the αvβ3 antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammatory arthritis, and inhibition of cancer or metastatic tumor growth. Most preferably, the αvβ3 antagonizing effect is inhibition of bone resorption. Alternatively, the αv integrin antagonizing effect is an αvβ5 antagonizing effect or a dual αvβ3/αvβ5 antagonizing effect. Examples of αvβ5 antagonizing effects are inhibition of restenosis, atherosclerosis, angiogenesis, diabetic retinopathy, macular degeneration, inflammatory arthritis, cancer, and metastatic tumor growth.

Additional examples of the invention are methods of inhibiting bone resorption and of treating and/or preventing osteoporosis in a mammal in need thereof, comprising administering to the mammal a therapeutically effective amount of the compounds or any of the pharmaceutical compositions decribed above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of the compounds or any of the pharmaceutical compositions described above.

More particularly exemplifying the invention is the use of the compounds described above in the preparation of a medicament for the treatment and/or prevention of osteoporosis in a mammal in need thereof. Still further exemplifying the invention is the use of the compounds described above in the preparation of a medicament for the treatment and/or prevention of bone resorption, metastatic tumor growth, cancer, restenosis, atherosclerosis, diabetic retinopathy, macular degeneration, inflammatory arthritis, and/or angiogenesis.

Also exemplifying the invention are compositions further comprising an active ingredient selected from the group consisting of a) an organic bisphosphonate or a pharmaceutically acceptable salt or ester thereof,
b) an estrogen receptor modulator,
c) an androgen receptor modulator,
d) a cytotoxic/antiproliferative agent,
e) a matrix metalloproteinase inhibitor,
f) an inhibitor of epidermal-derived, fibroblast-derived, or platelet-derived growth factors,
g) an inhibitor of VEGF,
h) an antibody to a growth factor or to a growth factor receptor,
i) an inhibitor of Flk-1/KDR, Flt-1, Tck/Tie-2, or Tie-1,
j) a cathepsin K inhibitor,
k) a growth hormone secretagogue,
l) an inhibitor of osteoclast proton ATPase,
m) an inhibitor of urokinase plasminogen activator (u-PA),
n) a tumor-specific antibody-interleukin-2 fusion protein, o) an inhibitor of HMG-CoA reductase,
p) a farnesyl transferase inhibitor or a geranylgeranyl transferase inhibitor or a dual farnesyl/geranylgeranyl transferase inhibitor, and
q) a parathyroid hormone (PTH) analog;
and mixtures thereof.
(See, B. Millauer et al., "Dominant-Negative Inhibition of Flk-1 Suppresses the Growth of Many Tumor Types in Vivo", *Cancer Research,* 56, 1615–1620 (1996), which is incorporated by reference herein in its entirety).

Preferably, the active ingredient is selected from the group consisting of:
a) an organic bisphosphonate or a pharmaceutically acceptable salt or ester thereof,
b) an estrogen receptor modulator,
c) an androgen receptor modulator,
d) an inhibitor of osteoclast proton ATPase,
e) a parathyroid hormone (PTH) analog, and
f) a cathepsin K inhibitor; and mixtures thereof.

Nonlimiting examples of such bisphosphonates include alendronate, cimadronate, clodronate, etidronate, ibandronate, pamidronate, piridronate, risedronate, tiludronate, and zolendronate, and pharmaceutically acceptable salts and esters thereof. A particularly preferred bisphosphonate is alendronate, especially alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

Members of the class of HMG-CoA reductase inhibitors, known as the "statins," have been found to trigger the growth of new bone, replacing bone mass lost as a result of osteoporosis (see *The Wall Street Journal,* Friday, Dec. 3, 1999, page B1). Therefore, the statins hold promise for the treatment of bone resorption. Nonlimiting examples of statins are lovastatin, simvastatin, atorvastatin, pravastatin, fluvastatin, cerivastatin, and rosuvastatin.

Evidence for crucial role of the urokinase-urokinase receptor (u-PA-u-PAR) in angiogenesis, tumor invasion, inflammation, and matrix remodeling during wound healing and development has been presented [see Y. Koshelnick et al., "Mechanisms of signaling through Urokinase Receptor and the Cellular Response," *Thrombosis and Haemostasis* 82: 305–311 (1999) and F. Blasi, "Proteolysis, Cell Adhesion, Chemotaxis, and Invasiveness Are Regulated by the u-PA-u-PAR-PAI-1 System," *Thrombosis and Haemostasis* 82: 298–304 (1999)]. Thus, specific antagonists of the binding of u-PA to u-PAR inhibit cell-surface plasminogen activation, tumor growth, and angiogenesis in both in vitro and in vivo models.

H. N. Lode and coworkers in *PNAS USA* 96: 1591–1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth.

The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases (see C. Farina et al., "Selective inhibitors of the osteoclast vacuolar proton ATPase as novel bone antiresorptive agents," *DDT,* 4: 163–172 (1999)).

Evidence has been presented that androgenic steroids play a physiological role in the development of bone mass in men and women and that androgens act directly on bone. Androgen receptors have been demonstrated in human osteoblast-like cell lines and androgens have been shown to directly stimulate bone cell proliferation and differentiation. For a discussion, reference is made to S. R. Davis, "The therapeutic use of androgens in women," *J. Steroid Biochem. Mol. Biol.,* 69: 177–184 (1999) and K. A. Hansen and S. P. T. Tho, "Androgens and Bone Health," *Seminars in Reproductive Endocrinology,"* 16: 129–134 (1998). Thus, androgen receptor modulators may have utility in the treatment and prevention of bone loss in women.

The angiogenic factor VEGF has been shown to stimulate the bone-resorbing activity of isolated mature rabbit osteoclasts via binding to its receptors on osteoclasts (see M. Nakagawa et al., "Vascular endothelial growth factor (VEGF) directly enhances osteoclastic bone resorption and survival of mature osteoclasts," *FEBS Letters,* 473: 161–164 (2000)). Therefore, the development of antagonists of VEGF binding to osteoclast receptors, such as KDR/Flk-1 and Flt-1, may provide yet a further approach to the treatment or prevention of bone resorption.

Activators of the peroxisome proliferator-activated receptor-γ (PPARγ), such as the thiazolidinediones (TZD's), inhibit osteoclast-like cell formation and bone resorption in vitro. Results reported by R. Okazaki et al. in *Endocrinology,* 140, pp 5060–5065, (1999) point to a local mechanism on bone marrow cells as well as a systemic one on glucose metabolism. Nonlimiting examples of PPARγ activators include troglitazone, pioglitazone, rosiglitazone, and BRL 49653.

The use of parathyroid hormone (PTH) for the treatment of osteoporosis has been suggested in the art. PTH has been found to increase the activity of osteoblasts, the cells that form bone, thereby promoting the synthesis of new bone (*Modem Drug Discovery,* Vol. 3, No. 8, 2000). In studies reported at the First World Congress on Osteoporosis held in Chicago in June 2000, women in combined PTH-estrogen therapy exhibited a 12.8% increase in spinal bone mass and a 4.4% increase in total hip mass. Another study presented at the same meeting showed that PTH could increase bone size as well as density. A clinical trial of the effect of the human parathyroid hormone 1–34 fragment [hPTH(1–34)] on postmenopausal osteoporotic women resulted in ≧65% reduction in spine fractures and a 54% reduction in nonvertebral fractures, after a median of 22 months of treatment [see J. M. Hock, *Bone,* 27: 467–469 (2000) and S. Mohan, et al., *Bone,* 27: 471–478 (2000), and references cited therein]. Thus, PTH and fragments thereof, such as hPTH (1–34), may prove to be efficacious in the treatment of osteoporosis alone or in combination with other agents, such as the αvβ3 integrin antagonists of the present invention.

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate, an estrogen receptor modulator, an androgen receptor modulator, a cathepsin K inhibitor, an HMG-CoA reductase inhibitor, a PPARγ activator, a VEGF receptor antagonist, an inhibitor of the osteoclast proton ATPase, or a PTH analog.

Additional illustrations of the invention are methods of treating cancer or metastatic tumor growth in a mammal in need thereof, comprising administering to the mammal a therapeutically effective amount of a compounds described above and one or more agents known to be cytotoxic/antiproliferative. Also, the compounds of the present invention can be administered in combination with radiation therapy for treating cancer and metastatic tumor growth.

In addition, the integrin αvβ3 antagonist of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid-induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an αvβ3 receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, it may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compounds desired can be employed as an αvβ3 antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, the compound of the present invention may be administered in a single daily dose, or the total daily dosage may be administered in divided doses of two, three or four times daily. Furthermore, the compound of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and is typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the Schemes and Examples below, various reagent symbols and abbreviations have the following meanings:

| | |
|---|---|
| AcOH: | Acetic acid |
| Ar: | Argon |
| 9-BBN: | 9-Borabicyclo[3.3.1]nonane |
| BOC(Boc): | t-Butyloxycarbonyl |
| CBZ(Cbz): | Carbobenzyloxy or benzyloxycarbonyl |
| CH$_2$Cl$_2$: | Methylene chloride |
| CH$_3$CN: | Acetonitrile |
| CHCl$_3$: | Chloroform |
| DIAD: | Diisopropyl azodicarboxylate |
| DIPEA: | Diisopropylethylamine |
| DMAP: | 4-Dimethylaminopyridine |
| DMF: | N,N-Dimethylformamide |
| DMSO: | Dimethylsulfoxide |
| DPPF: | 1,1'-Bis(diphenylphosphino)ferrocene. |
| EtOAc: | Ethyl acetate |
| EtOH: | Ethanol |
| HPLC: | High-performance liquid chromatography |
| K$_2$CO$_3$: | Potassium carbonate |
| LDA: | Lithium diisopropylamide |
| MeOH: | Methanol |
| MgSO$_4$: | Magnesium sulfate |
| NEt$_3$: | Triethylamine |
| NMM: | N-methylmorpholine |
| Pd/C: | Palladium on activated carbon catalyst |
| PPh$_3$: | Triphenylphosphine |
| Ph: | Phenyl |
| RT: | Room temperature |
| pTSA | p-Toluenesulfonic acid |
| TEA: | Triethylamine |
| TFA: | Trifluoroacetic acid |
| THF: | Tetrahydrofuran |
| TLC: | Thin Layer Chromatography |

The compounds of structural formula I can be prepared by the procedures detailed in Schemes and the Examples below. Those skilled in the art will readily understand that known variations of the conditions and processes of the following preparative procedures can be used to prepare the compounds. Unless stated otherwise, all operations were carried out at room or ambient temperature, and all temperatures are degrees Celsius.

EXAMPLE 1

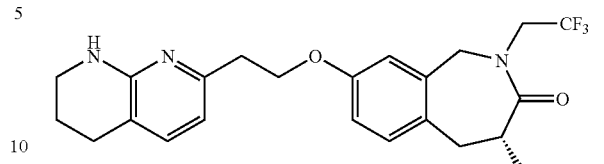

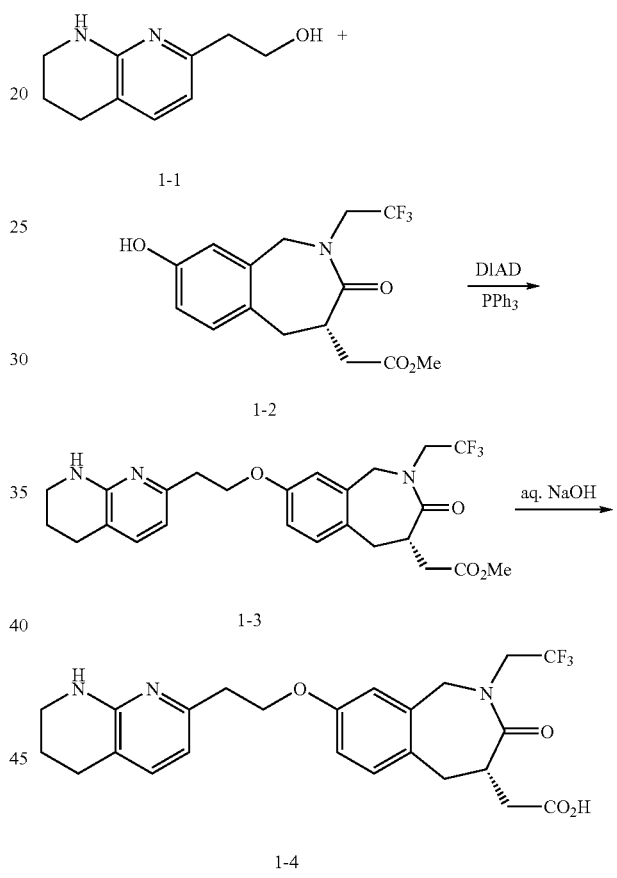

Step A: Methyl (4S)-3-oxo-8-[2-(5,6,7,8-tetrahydro-1,8-nalphthyridin-2-yl)ethoxy]-2-(2,2,2-trifluoroethyl)-2,3,4,5-tetrahydro-1H-2-benzazepin-4-acetate (1-3)

A solution of 1-1 (0.216 g, 1.21 mmol; prepared as described in WO 99/45927), 1-2 (0.40 g, 1.21 mmol; prepared as described in WO 98/14192), and triphenylphosphine (0.38 g, 1.45 mmol) in 9:1 THF/DMF (5 mL) was cooled to 0° C., and diisopropyl azodicarboxylate (DIAD) (0.285 mL, 1.45 mmol) was slowly added. The mixture was allowed to warm to ambient temperature and stir for 15 hours, then concentrated. Silica gel chromatography (0–5% MeOH/EtOAc) provided 1-3 as a colorless oil (70 mg).

Mass spectrum: Calculated for C$_{25}$H$_{28}$F$_3$N$_3$O$_4$: 491.2; found: 492.1 (M+H).

Step B: (4S)-3-Oxo-8-[2-(5,6,7,8-tetrahydro-1,8-naphthyridin-2-yl)ethoxy]-2-(2,2,2-trifluoroethyl)-2,3,4,5-tetrahydro-1H-2-benzazepin-4-acetic acid (1-4)

To a solution of 1-3 in dioxane (2 mL) was added NaOH (0.60 mL of 1.0 N in water). After 3 hours, an additional 0.6 mL of the NaOH solution was added. After a further 6 hours, HCl (1.2 mL 1.0 N in water) was added, and the mixture concentrated to dryness. Silica gel chromatography (20:10:1:1 to 10:10:1:1 EtOAc/EtOH/H₂O/NH₄OH) provided 1-4 as a colorless solid (62 mg).

Mass spectrum: Calculated for $C_{24}H_{26}F_3N_3O_4$: 477.2; found: 478.1 (M+H). $^1$H NMR (CD₃OD): δ 7.31 (1H, d, J=7.3 Hz), 7.01 (1H, d, J=8.5 Hz), 6.78 (1H, d, J=8.5 Hz), 6.72 (1H, s), 6.55 (1H, d, J=7.3 Hz), 5.32 (1H, d, J=16.6 Hz), 4.29–4.21 (3H, m), 4.32–4.05 (2H, m), 3.81 (1H, m), 3.42 (2H, m), 3.06–2.99 (3H, m), 2.86–2.78 (1H, m), 2.76–2.72 (3H, m), 2.42 (1H, m), 1.89 (2H, m).

EXAMPLE 2

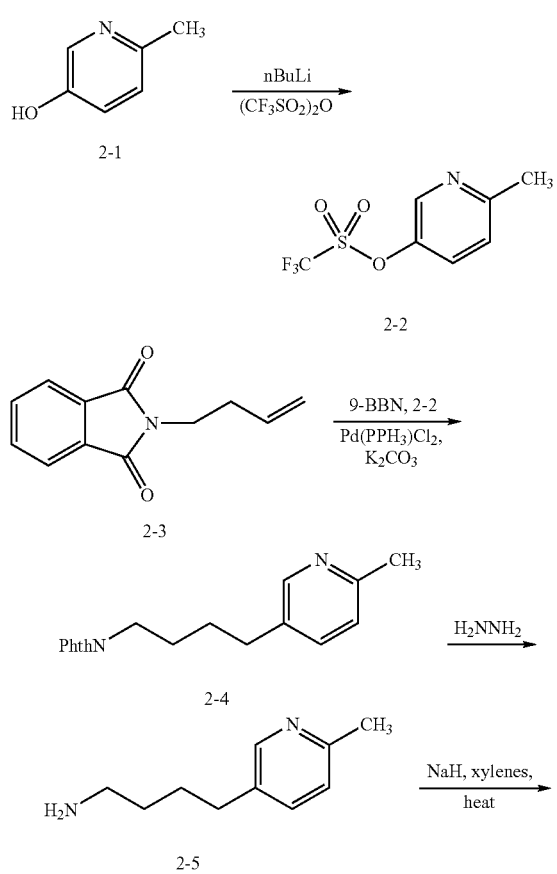

SCHEME 2

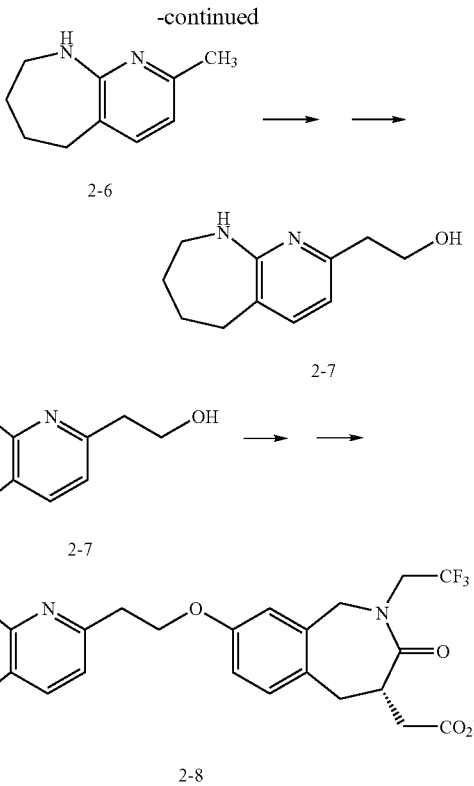

6-(Methylpyridin-3-yl) trifluoromethanesulfonate (2-2)

To a suspension of 2-methyl-5-hydroxypyridine (2-1, 5 g, 46 mmol) in THF (50 mL) at −78° C. was added dropwise n-butyllithium (18.3 mL of 2.5 M in hexanes, 46 mmol), producing a clear solution. Trifluoromethanesulfonic anhydride (7.69 mL, 46 mmol) was then added dropwise, producing a deep red-colored solution. After 0.25 hours, the reaction was quenched by the addition of 100 mL of 1N NaOH. The mixture was diluted with ether, separated, and the organics washed with water, then dried over magnesium sulfate. Evaporation of the solvents produced 2-2 as a red oil (6.1 g).

$^1$H NMR (CDCl₃): δ 8.48 (s, 1H), 7.56 (m, 1H), 7.24 (m, 1H), 2.62 (s, 3H).

2-(But-3-enyl)-isoindole-1,3-dione (2-3)

To a stirred solution of 4-bromo-1-butene (20 g, 148 mmol) in DMF (150 mL) was added potassium phthalimide (25 g, 133 mmol) and the mixture stirred for 18 hours at 70° C. After cooling to RT, the mixture was diluted with ether, washed with water and brine, dried over MgSO₄, and concentrated to give 2-3 as a white solid.

$^1$H NMR (400 MHz, CDCl₃): δ 7.85 (m, 2H), 7.72 (m, 2H), 5.82 (m, 1H), 5.08 (m, 2H), 3.77 (t, 2H, J=7 Hz), 2.44 (m, 2H).

2-[4-(6-Methylpyridin-3-yl)butyl]-1H-isoindole-1,3(2H)-dione (2-4)

To a suspension of 2-3 (12.7 g, 63.2 mmol) was added a solution of 9-BBN in THF (132 mL of a 0.5 M solution, 65.8 mmol). After stirring for 15 hours, potassium carbonate powder (14.5 g, 105 mmol) and 2-3 (12.7 g, 52.7 mmol) was added. To this mixture was then added a premixed, degassed, aged (80° C. for 30 minutes with vigorous stirring) suspension of Pd(OAc)₂ (1.78 g, 7.9 mmol) and DPPF (4.96 g, 8.9 mmol) in DMF (50 mL) via a cannula, and the resulting mixture degassed with argon bubbling for 30 minutes. The mixture was then heated at 70° C. for 3 hours. Following cooling, the mixture was reduced to a thick slurry, diluted with ether, washed with water and brine. The organics were dried over MgSO₄ and concentrated to give a brown oil. This residue was chromatographed on silica gel (40–60% EtOAc/hexanes) to give 2-4 (9.6 g) as a yellow solid.

$^1$H NMR (400 MHz, CDCl₃): δ 8.32 (s, 1H), 7.83 (d, 2H), 7.73 (d, 2H), 7.38 (m, 1H), 7.02 (d, 1H), 3.70 (t, 2H), 2.62 (t, 2H), 2.43 (s, 3H), 1.74 (m, 2H), 1.66 (m, 2H).

4-(6-Methylpyridin-3-yl)butan-1-amine (2-5)

A mixture of 2-4 (7.2 g, 24.5 mmol), hydrazine (3.8 mL), and ethanol (500 mL) was heated at reflux for 4 hours. The resulting mixture was cooled and filtered, and the filtrate concentrated to give 2-5 as a yellow solid (4.7 g) contaminated with some phthalhydrazide.

$^1$H NMR (400 MHz, CDCl₃): δ 8.30 (s, 1H), 7.37 (m, 1H), 7.03 (m, 1H), 2.82 (br s, 2H), 2.78 (t, 2H), 2.58 (t, 2H), 2.52 (s, 3H), 1.68 (m, 2H), 1.54 (m, 2H).

2-Methyl-6.7,8,9-tetrahydro-5H-pyido[2.3-b]azepine (2-6)

A mixture of 2-5 (4.02 g, 24.5 mmol), sodium hydride (2.93 g of 60% in mineral oil, 73.4 mmol), and xylenes (100 mL) was stirred for 30 minutes and purged with argon, then heated at 130° C. for 4 days. The mixture was quenched with 10% potassium carbonate, diluted with ethyl acetate, and washed with brine. The organics were dried over MgSO₄ and concentrated. This residue was chromatographed on silica gel (0–100% EtOAc/hexanes) to give 2-6 (2.2 g) as a yellow solid.

$^1$H NMR (400 MHz, CDCl₃): δ 8.32 (s, 1H), 7.83 (d, 2H), 7.73 (d, 2H), 7.38 (m, 1H), 7.02 (d, 1H), 3.70 (t, 2H), 2.62 (t, 2H), 2.43 (s, 3H), 1.74 (m, 2H), 1.66 (m, 2H).

Utilizing the procedures for the preparation of 1-1 disclosed in WO 99/45927, 2-6 was then converted to 2-7. Then 2-7 was converted to 2-8 using the method for the preparation of 1-4 from 1-1 described in Scheme 1.

[(4S)-3-Oxo-8-[2-(6,7,8,9-tetrahydro-5H-pyrido[2,3-b]azepin-2-yl)ethoxy]-2-(2,2,2-trifluoroethyl)-2,3,4,5-tetrahydro-1H-2-benzazepin-4-yl]acetic acid (2-8)

$^1$H NMR (CD₃OD): δ 7.38 (d, 1H), 7.02 (d, 1H), 6.78 (d, 1H), 6.72 (m, 2H), 5.32 (d, 1H), 4.26 (m, 3H), 4.12 (m, 2H), 3.81 (s, 1H), 3.19 (m, 2H), 3.06 (m, 3H), 2.88–2.71 (m, 4H), 2.48 (s, 1H), 1.84 (m, 2H), 1.75 (m, 2H). Mass spectrum: Calculated for C₂₄H₂₆F₃N₃O₄: 491.5; found: 492.1 (M+H).

EXAMPLE 3

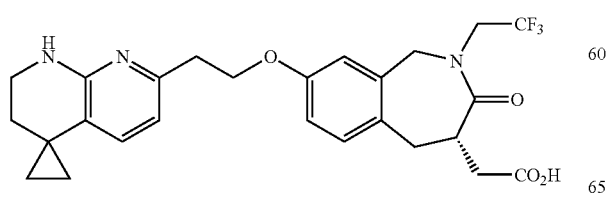

Example 3 (Compound 3-13) is Prepared as Outlined in SCHEME 3.

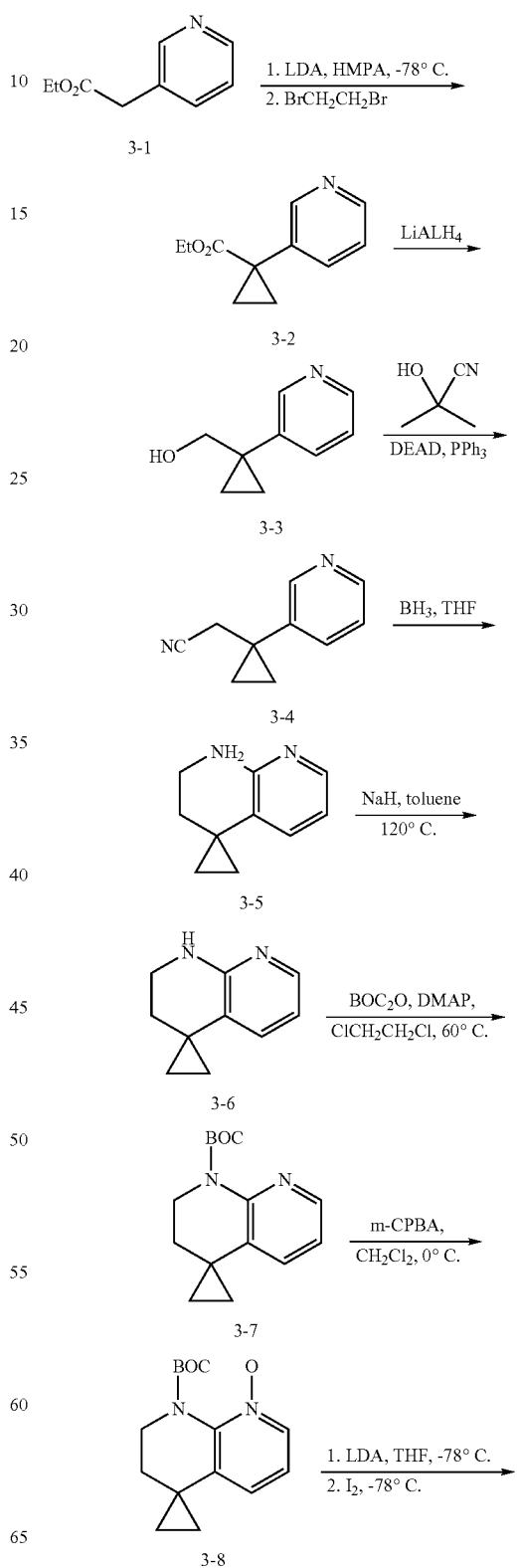

-continued
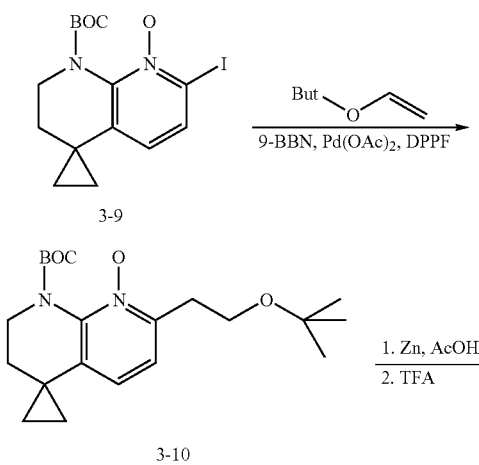
3-9
3-10
3-11
3-12
-continued
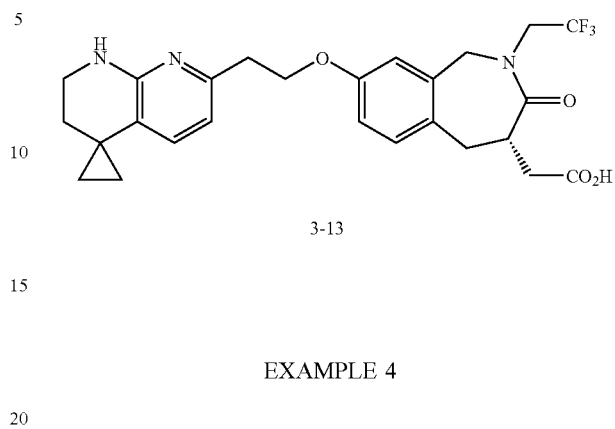
3-13
EXAMPLE 4
Example 4 (Compound 4-7) is Prepared as Outlined in SCHEME 4.
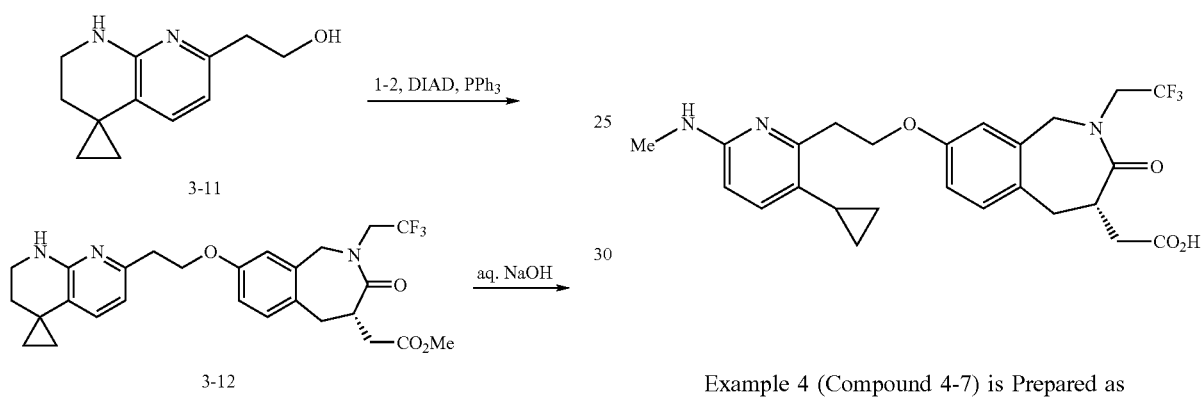
SCHEME 4
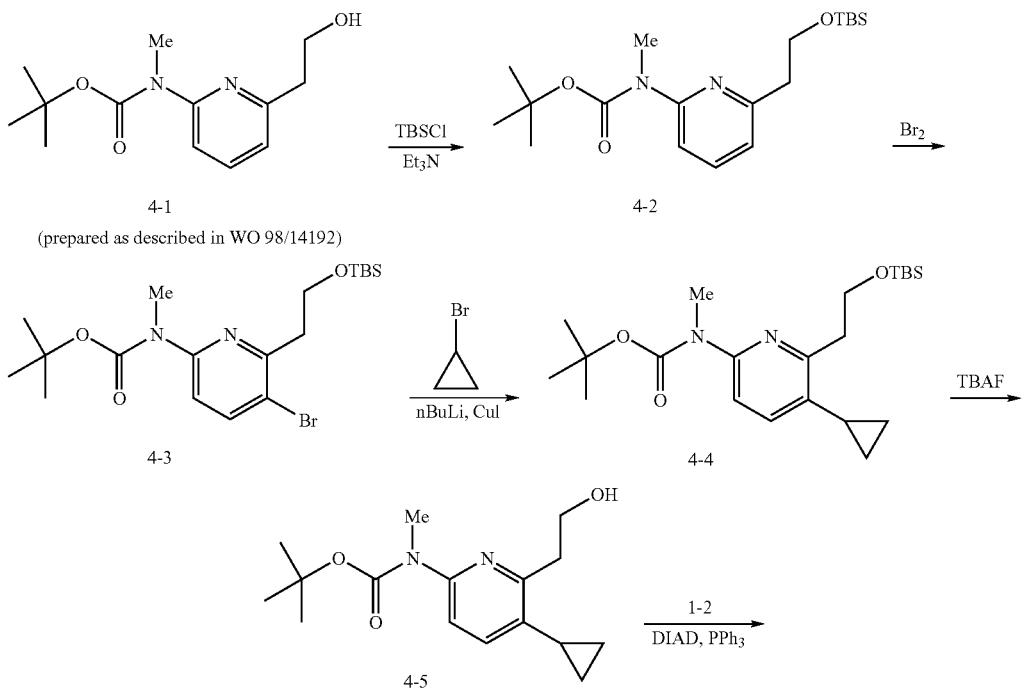
4-1
(prepared as described in WO 98/14192)
4-2
4-3
4-4
4-5

-continued
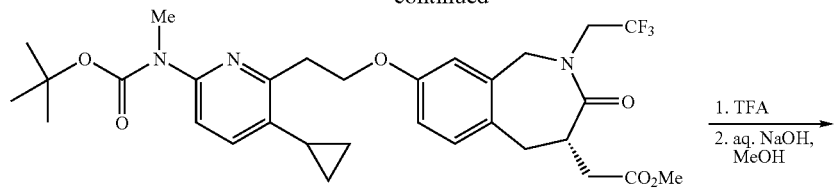
1. TFA
2. aq. NaOH, MeOH
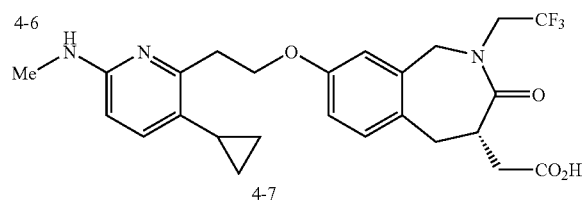
4-7
SCHEME A
Synthesis of Radioligand for SPAV3 Assay
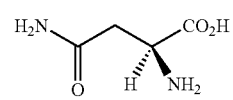
A-1
| NaOH, dioxane, H₂O
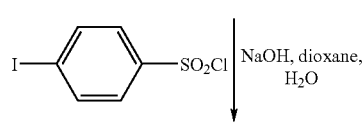
A-2
1. Br₂, NaOH, H₂O
2. HCl
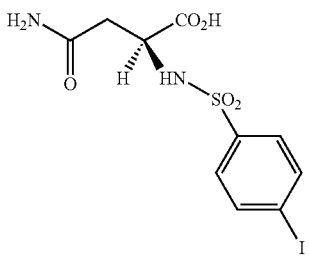
A-3
 HCl
EtOH
-continued
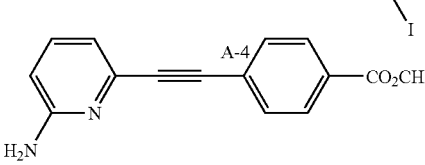
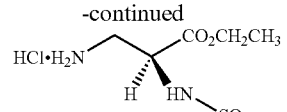
A-4
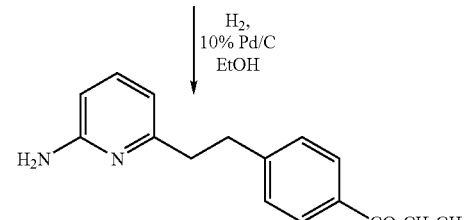
A-5
H₂, 10% Pd/C
EtOH
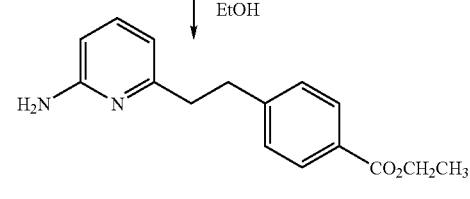
A-5a
6N HCl
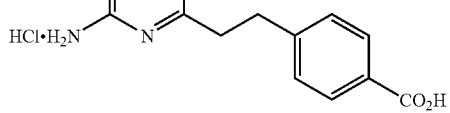
A-6
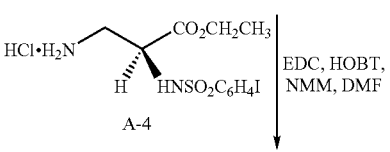 EDC, HOBT, NMM, DMF
A-4

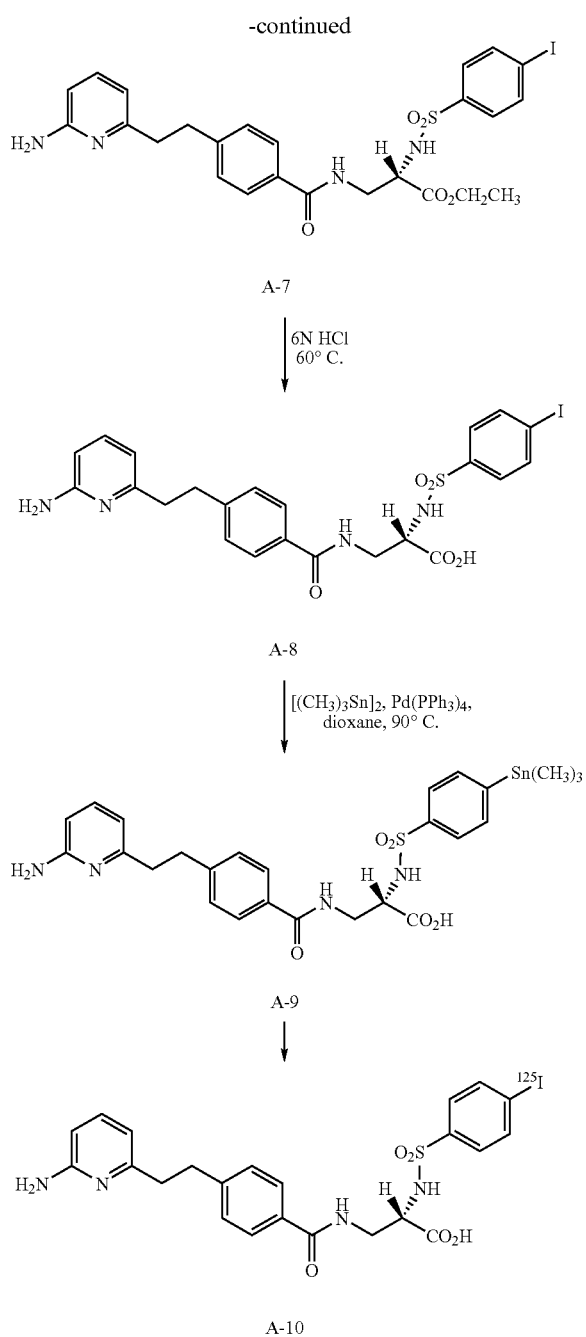

2(S)-(4-Iodo-phenylsulfonylamino)-β-alanine (A-3)

To a stirred solution of NaOH (7.14 g, 181.8 mmol) and H$_2$O (40 ml) at 0° C. was added Br$_2$ (1.30 ml, 24.9 mmol) dropwise over a ten minute period. After ~5 minutes, acid A-2 (9.9 g, 24.9 mmol), NaOH (2.00 g, 49.8 mmol) and H$_2$O (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid A-3 as a white solid.

$^1$H NMR (300 MHz, D$_2$O) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (A-4)

HCl gas was rapidly bubbled through a suspension of acid A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.

$^1$H NMR (300 MHz, CD$_3$OD) δ 7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7=Hz).

Ethyl 4-[2-(2-Aminopyridin-6-yl)ethyl]benzoate (A-5a)

A mixture of ester A-5 (700 mg, 2.63 mmol), (for preparation, see: Scheme 29 (intermediate 29-3) of U.S. Pat. No. 5,741,796 (Apr. 21, 1998)), 10% Pd/C (350 mg) and EtOH were stirred under 1 atm H$_2$. After 20 h, the reaction was filtered through a celite pad and then concentrated to provide ester A-5a as a brown oil.

TLC R$_f$=0.23 (silica, 40% EtOAc/hexanes)

$^1$H NMR (300 MHz, CDCl$_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (A-6)

A suspension of ester A-5a (625 mg, 2.31 mmol) in 6N HCl (12 ml) was heated to 60° C. After ~20 h, the reaction was concentrated to give acid A-6 as a tan solid.

$^1$H NMR (300 MHz, CD$_3$OD) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopydin-6-yl)ethyl]benzoyl-2(S)-(4-iodo-phenylsulfonylamino)-D-alanine (A-7)

A solution of acid 15-6 (400 mg, 1.43 mmol), amine A-4 (686 mg, 1.57 mmol), EDC (358 mg, 1.86 mmol), HOBT (252 mg, 1.86 mmol), NMM (632 µl, 5.72 mmol) in DMF (10 ml) was stirred for ~20 h. The reaction was diluted with EtOAc and then washed with sat. NaHCO$_3$, brine, dried (MgSO$_4$) and concentrated. Flash chromatography (silica, EtOAc then 5% isopropanol/EtOAc) provided amide A-7 as a white solid.

TLC R$_f$=0.4 (silica, 10% isopropanol/EtOAc)

$^1$H NMR (300 MHz, CD$_3$OD) δ 7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopydin-6-yl)ethyl]benzoyl-2(S)-(4-iodophenyl-sulfonylamino)-β-alanine (A-8)

A solution of ester A-7 (200 mg, 0.3213 mmol) and 6N HCl (30 ml) was heated to 60° C. After ~20 h, the reaction N-(4-Iodo-phenylsulfonylamino)-L-asparagine (A-2)

To a stirred solution of acid A-1 (4.39 g, 33.2 mmol), NaOH (1.49 g, 37.2 mmol), dioxane (30 ml) and H$_2$O (30 ml) at 0° C. was added pipsyl chloride (10.34 g, 34.2 mmol). After ~5 minutes, NaOH (1.49, 37.2 mmol) dissolved in 15 ml H$_2$O, was added followed by the removal of the cooling bath. After 2.0 h, the reaction mixture was concentrated. The residue was dissolved in H$_2$O (300 ml) and then washed with EtOAc. The aqueous portion was cooled to 0° C. and then acidified with concentrated HCl. The solid was collected and then washed with Et$_2$O to provide acid A-2 as a white solid.

$^1$H NMR (300 MHz, D$_2$O) δ 7.86 (d, 2H, J=8 Hz), 7.48 (d, 2H, J=8 Hz) 3.70 (m, 1H), 2.39 (m, 2H).

mixture was concentrated. Flash chromatography (silica, 20:20:1:1 EtOAc/EtOH/NH$_4$OH/H$_2$O) provided acid A-8 as a white solid.
TLC R$_f$=0.45 (silica, 20:20:1:1 EtOAc/EtOH/NH$_4$OH/H$_2$O)
$^1$H NMR (400 MHz, DMSO-d$_6$) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl]benzoyl-2(S)-(4-trimethylstannyl-phenylsulfonylamino-β-alanine (A-9)

A solution of iodide A-8 (70 mg, 0.1178 mmol), [(CH$_3$)$_3$Sn]$_2$ (49 μl, 0.2356 mmol), Pd(PPh$_3$)$_4$ (5 mg) and dioxane (7 ml) was heated to 90° C. After 2 h, the reaction was concentrated and then purified by preparative HPLC (Delta-Pak C$_{18}$ 15 μM 100 A°, 40×100 mm; 95:5 then 5:95H$_2$O/CH$_3$CN) to provide the trifluoroacetate salt. The salt was suspended in H$_2$O (10 ml), treated with NH$_4$OH (5 drops) and then lyophilized to provide amide A-9 as a white solid.
$^1$H NMR (400 MHz, DMSO-d$_6$) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodo-phenylsulfonylamino-β-alanine (A-10)

An iodobead (Pierce) was added to a shipping vial of 5 mCi of Na$^{125}$I (Amersham, IMS30) and stirred for five minutes at room temperature. A solution of 0.1 mg of A-9 in 0.05 mL of 10% H$_2$SO$_4$/MeOH was made and immediately added to the Na$^{125}$I/iodobead vial. After stirring for three minutes at room temperature, approximately 0.04–0.05 mL of NH$_4$OH was added so the reaction mixture was at pH 6-7. The entire reaction mixture was injected onto the HPLC for purification [Vydac peptide-protein C-18 column, 4.6×250 mm, linear gradient of 10% acetonitrile (0.1% (TFA):H$_2$O (0.1% TFA) to 90% acetonitrile (0.1% TFA):H$_2$O (0.1% TFA) over 30 minutes, 1 mUmin]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

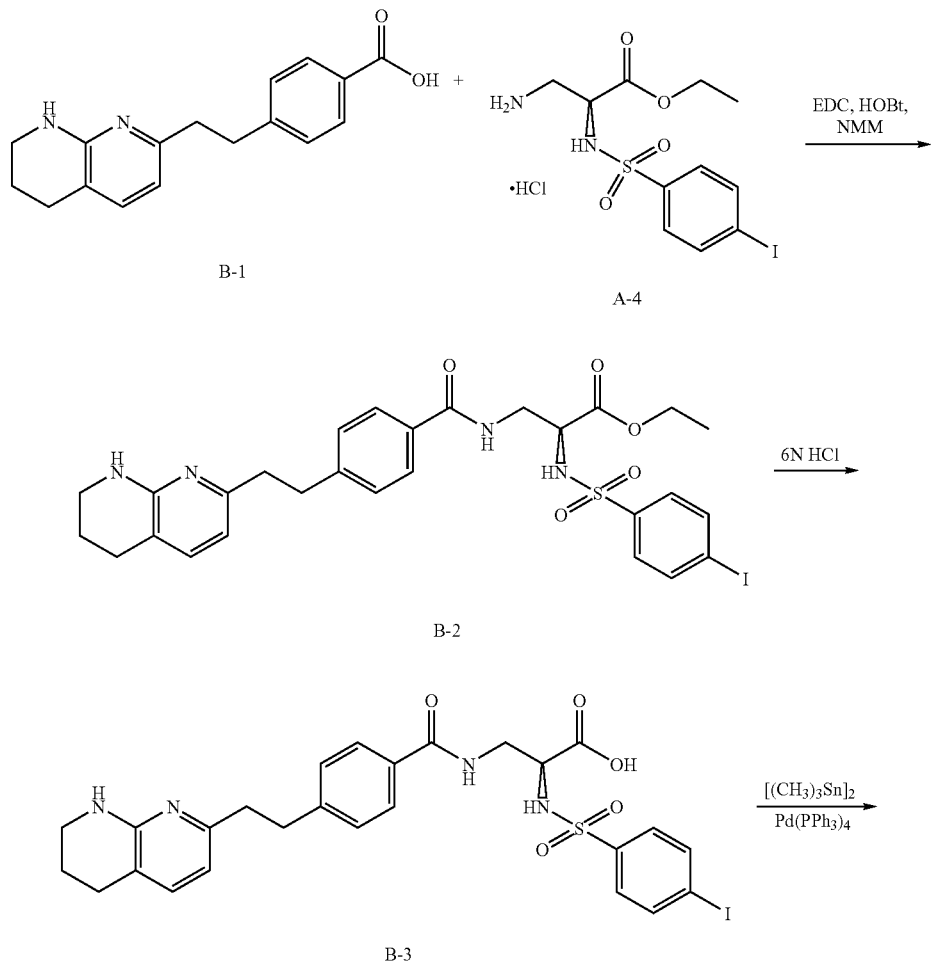

SCHEME B
Synthesis of Radioligand for SPAV5 Assay

-continued

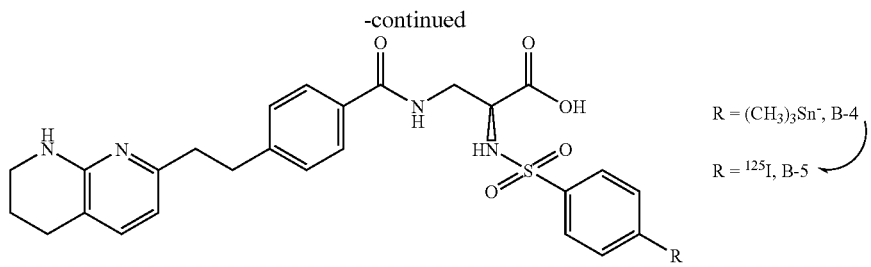

2(S)-(4-Iodo-benzenesulfonylamino)-3-{4-[2-(5,6,7,8-tetrahydro-[1,8]naphthyridin-2-yl)-ethyl]-benzoylamino}-propionic acid ethyl ester (B-2)

A mixture of B-1 (0.23 g, 0.72 mmol; for preparation see U.S. Pat. No. 5,741,796), A-4 (0.343 g, 0.792 mmol), EDC (0.179 g, 0.93 mmol), HOBT (0.126 g, 0.93 mmol), NMM (0.316 mL, 2.86 mmol) in acetonitrile (3 mL) and DMF (3 mL) was stirred for 2 hours at ambient temperature then diluted with ethyl acetate, washed with water, saturated aqueous $NaHCO_3$, and brine, dried over $MgSO_4$, and concentrated. The residue was chromatographed on silica gel (70:25:5 $CHCl_3$/EtOAc/MeOH) to give B-2 as a white solid. TLC $R_f$=0.22 (silica, 70:25:5 $CHCl_3$/EtOAc/MeOH).

$^1$H NMR (300 MHz, $CDCl_3$) δ 7.79 (d, 2H, J=8 Hz), 7.63 (d, 2H, J=8 Hz), 7.54 (d, 2H, J=8 Hz), 7.27 (d, 2H, J=8 Hz),7.04 (d, 1H, J=7 Hz), 6.60 (m, 1H), 6.29 (d, 1H, J=7 Hz), 4.83 (br s, 1H), 4.09 (m, 3H), 3.84 (m, 1H), 3.68 (m, 1H), 3.42 (m, 2H), 3.01 (m, 4H), 2.86 (m, 4H), 2.69 (t, 2H, J=6 Hz), 1.88 (m, 2H).

2(S)-(4-Iodo-benzenesulfonylamino)-3-{4-[2-(5,6,7,8-tetrahydro-[1,8]naphthyridin-2-yl)-ethyl]-benzoylamino}-propionic acid (B-3)

A mixture of B-2 (0.38 g, 0.573 mmol) and 6N HCl (50 mL) was stirred for 14 hours at 60° C. After cooling to room temperature, the mixture was concentrated, and the residue chromatographed on silica gel (25:10:1:1 to 15:10:1:1 EtOAc/EtOH/$NH_4OH$/$H_2O$) to give B-3 as a white solid. TLC $R_f$=0.43 (silica, 10:10:1:1 EtOAc/EtOH/$NH_4OH$/$H_2O$).

$^1$H NMR (300 MHz, DMSO-$d_6$) δ 8.42 (m, 1H), 7.79 (d, 2H, J=8 Hz), 7.63 (d, 2H, J=8 Hz), 7.44 (d, 2H, J=8 Hz), 7.27 (d, 2H, J=8 Hz),7.10 (d, 1H, J=7 Hz), 6.58 (br s, 1H), 6.32 (d, 1H, J=7 Hz), 3.96 (m, 1H), 3.51 (m, 1H), 3.30 (m, 5H), 2.96 (m, 2H), 2.78 (m, 2H), 2.62 (m, 2H), 1.77 (m, 2H).

HRMS: For $C_{26}H_{27}N_4O_5S$, expected 635.0818, found 635.0831.

3-4-[2-(5,6,7,8-Tetrahydro-[1,8]naphthyridin-2-yl)-ethyl]-benzoylamino]-2(S)-(4-trimethylstannanyl-benzenesulfonylamino)-propionic acid (B4)

A mixture of B-3 (0.10 g, 0.16 mmol), hexamethyldistannane (0.065 mL, 0.32 mmol), Pd(PPh$_3$)$_4$, and dioxane (10 mL) was stirred for one hour at 90° C. After cooling to room temperature, the mixture was concentrated, and the residue chromatographed on silica gel (50:10:1:1 to 25:10:1:1 EtOAc/EtOH(NH$_4$H/H$_2$O) to give B-4 as a white solid. TLC $R_f$=0.48 (silica, 15:10:1:1 EtOAc/EtOH/NH$_4$OH/H$_2$O).

$^1$H NMR (300 MHz, DMSO-$d_6$) δ 8.38 (m, 1H), 8.14 (m, 1H), 7.63 (m, 4H), 7.28 (d, 2H, J=8 Hz), 7.08 (d, 1H, J=7 Hz), 6.50 (br s, 1H), 6.28 (d, 1H, J=7 Hz), 3.96 (m, 1H), 3.48 (m, 1H), 3.31 (m, 5H), 2.96 (m, 2H), 2.78 (m, 2H), 2.62 (m, 2H), 1.77 (m, 2H), 0.28 (s, 9H).

High resolution mass spectrum: For $C_{29}H_{36}N_4O_5SSn$, expected 665.1533 ($^{112}Sn$) and 673.1507 ($^{120}Sn$), found 665.1510 and 673.1505.

2(S)-(4-$^{125}$Iodo-benzenesulfonylamino)-3-{4-[2-(5,6,7,8-tetrahydro-[1,8]naphthyridin-2-yl)-ethyl]-benzoylamino}-propionic acid (B-5)

A stir bar, methanol (0.05 mL) and an iodobead (Pierce) were added to a shipping vial of Na$^{125}$, (10 mCi, Amersham, IMS300) and stirred for five minutes at room temperature. A solution of B-4 (~0.1 mg) in methanol (0.04 mL) was made and a portion (0.02 mL) was added to a mixture of H$_2$SO$_4$ (0.005 mL) in methanol (0.025 mL), and this solution was added immediately to the Na$^{125}$I/iodobead vial. After stirring for two minutes at room temperature, the reaction was quenched with NH$_4$OH (0.04–0.05 mL) and the entire reaction mixture was injected onto the HPLC for purification [Vydac peptide-protein C-18 column, 4.6×250 mm, linear gradient of 10% acetonitrile:H$_2$O (0.1% TFA) to 90% acetonitrile:H$_2$O (0.1% TFA) over 20 minutes, 1 mL min]. The retention time of B-5 is 16 minutes under these conditions. Fractions containing the majority of the radioactivity were pooled, lyophilized and diluted with ethanol to give approximately 1 mCi of B-5, which coeluted on HPLC analysis with an authentic sample of B-3.

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure αvβ3 and αvβ5 binding and the bone resorption inhibiting activity of the compound of the present invention are described below.

Bone Resorption-Pit Assay

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur diaphysis are cut with a low speed diamond saw (Isomet, Beuler, Ltd., Lake Bluff, E). Bone slices are pooled, placed in a 10% ethanol solution and refrigerated until further use.

Prior to experimentation, bovine bone slices are ultrasonicated twice, 20 minutes each in $H_2O$. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml αMEM, pH 6.9 containing 5% fetal bovine serum and 1% penicillin/streptomycin.

Long bones from 7–14 day old rabbits (New Zealand White Hare) are dissected, cleaned of soft tissue and placed in αMEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically ~$2 \times 10^7$ cells/ml). A cell suspension consisting of $5 \times 10^6$/ml in αMEM containing 5% fetal bovine serum, 10 nM $1,25(OH)_2D_3$, and pencillin-streptomycin is prepared. 200 ml aliquots are added to bovine bone slices (200 mm×6 mm) and incubated for 2 hrs. at 37° C. in a humidified 5% $CO_2$ atmosphere. The medium is removed gently with a micropipettor and fresh medium containing test compounds is added. The cultures are incubated for 48 hrs., and assayed for c-telopeptide (fragments of the al chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of $H_2O$, and the bone slices are then fixed for 20 minutes in 2.5% glutaraldehyde, 0.1 M cacodylate, pH 7.4. After fixation, any remaining cellular debris is removed by 2 min. ultrasonication in the presence of 0.25 M $NH_4OH$ followed by 2×15 min ultrasonication in $H_2O$. The bone slices are immediately stained for 6-8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting $IC_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp. 31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB Assay

Duong et al., *J. Bone Miner. Res.*, 8: S378 (1993), describes a system for expressing the human integrin αvβ3. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture:
1. 175 μl TBS buffer (50 mM Tris.HCl pH 7.2, 150 mM NaCl, 1% BSA, 1 mM $CaCl_2$, 1 mM $MgCl_2$).
2. 25 ml cell extract (dilute with 100 mM octylglucoside buffer to give 2000 cpm/25 μl).
3. $^{125}$I-echistatin (25 μl/50,000 cpm) (see EP 382 451).
4. 25 μl buffer (total binding) or unlabeled echistatin (non-specific binding).

The reaction mixture was then incubated for 1 h at room temp. The unbound and the bound αvβ3 were separated by filtration using a Skatron Cell Harvester. The filters (prewet in 1.5% poly-ethyleneimine for 10 mins) were then washed with the wash buffer (50 mM Tris HCl, 1 mM $CaCl_2/MgCl_2$, pH 7.2). The filter was then counted in a gamma counter.

SPAV3 Assay

Materials:
1. Wheat germ agglutinin Scintillation Proximity Beads (SPA): Amersham
2. Octylglucopyranoside: Calbiochem
3. BEPES: Calbiochem
4. NaCl: Fisher
5. $CaCl_2$: Fisher
6. $MgCl_2$: SIGMA
7. Phenylmethylsulfonylfluoride (PMSF): SIGMA
8. Optiplate: PACKARD
9. Compound A-10 (specific activity 500–1000 Ci/mmole)
10. test compound
11. Purified integrin receptor: αvβ3 was purified from 293 cells overexpressing αvβ3 (Duong et al., *J. Bone Min. Res.*, 8:S378, 1993) according to Pytela (Methods in Enzymology, 144:475, 1987)
12. Binding buffer: 50 mM HEPES, pH 7.8, 100 mM NaCl, 1 mM $Ca^{2+}/Mg^{2+}$, 0.5 mM PMSF
13. 50 mM octylglucoside in binding buffer: 50-OG buffer Procedure:
1. Pretreatment of SPA beads:

500 mg of lyophilized SPA beads were first washed four times with 200 ml of 50-OG buffer and once with 100 ml of binding buffer, and then resuspended in 12.5 ml of binding buffer.

2. Preparation of SPA beads and receptor mixture

In each assay tube, 2.5 μl (40 mg/ml) of pretreated beads were suspended in 97.5 μl of binding buffer and 20 ml of 50-OG buffer. 5 ml (~30 ng/μl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 μl of binding buffer and 25 μl of 50-OG buffer.

3. Reaction

The following were sequentially added into Optiplate in corresponding wells:
  (i) Receptor/beads mixture (75 μl)
  (ii) 25 μl of each of the following: compound to be tested, binding buffer for total binding or A-8 for non-specific binding (final concentration 1 μM)
  (iii) A-10 in binding buffer (25 μl, final concentration 40 μM)
  (iv) Binding buffer (125 μl)
  (v) Each plate was sealed with plate sealer from PACKARD and incubated overnight with rocking at 4° C.

4. Plates were counted using PACKARD TOPCOUNT

5. % inhibition was calculated as follows:
A=total counts
B=nonspecific counts
C=sample counts
% inhibition=$[\{(A-B)-(C-B)\}/(A-B)]/(A-B) \times 100$ OCFORM Assay Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 mm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1 \times 10^6$ cells/mL. 50 µL was added to each well of 1.8 cells to yield 50,000 cells/well and 1,25-dihydroxy-vitamin $D_3$ ($D_3$) was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing $D_3$ to quadruplicate wells. Compounds were added again after 48 h with fresh medium containing $D_3$. After an additional 48 h., the medium was removed, cells were fixed with 10% formaldehyde in phosphate buffered saline for 10 minutes at room temperature, followed by a 1-2 minute treatment with ethanol:acetone (1:1) and air dried. The cells were then stained for tartarate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells was counted in each well.

SPAV5 Assay

Materials:
1. Wheat germ agglutinin Scintillation Proximity Beads (SPA): Amersham
2. Octylglucopyranoside and Phorbo-12-myristate-13-acetate (PMA): Calbiochem
3. Tris-HCl, NaCl and $CaCl_2$: Fisher
4. Minimum Essential Media (MEM): Gibco/BRL
5. Fetal bovine serum (FBS): Hyclone
6. $MgCl_2$, $MnCl_2$, and Phenylmethylsulfonylfluoride (PMSF): SIGMA
7. Protease inhibitor cocktail tablets: Boehringer Mannheim.
8. Optiplate-96 wells: PACKARD
9. B-5 was used as radiolabeled ligand (specific activity 500–1000 Ci/mmole) and B-3 (2.5 µM) was used to achieve 100% inhibition.
10. Test compound.
11. HEK293 cells overexpressing $\alpha_v\beta_5$ integrins (Simon et al., J. Biol. Chem. 272, 29380–29389, 1997) are cultured in 150 mm dishes in 10% FBS/MEM media (Gibco/BRL).
12. Lysis buffer: 100 mM octylglucopyranoside, 50 mM Tris, pH 7.5, 100 mM NaCl, 1 mM $CaCl_2$, 1 mM $MgCl_2$, 0.5 mM PMSF and protease inhibitors (1 tablet/50 ml buffer).
13. Binding buffer: 50 mM Tris, pH 7.5, 100 mM NaCl, 1 mM $CaCl_2$ 1 mM $MgCl_2$ and 1 mM $MnCl_2$.
14. 50 mM octylglucopyranoside in binding buffer: 50-OG buffer Procedure:
1. $\alpha_v\beta_5$-cell lysates: HEK 293 cells expressing $\alpha_v\beta_5$ integrins were cultured until confluent. Cells were then starved overnight in media containing 0.5% FBS, followed by treatment with 100 nM PMA for 20 min. Cells were washed 2 times with cold phosphate buffer saline (4° C.) and solubilized in lysis buffer for 30 min on ice. Lysates were clarified using a Beckman JA-20 at 20,000× g. Protein concentration of clarified lysates was determined using a micro BCA kit (Pierce) and stored in aliquots at 80° C.
2. Pretreatment of SPA beads:
500 mg of lyophilized SPA beads were first washed four times with 200 ml of 50-OG buffer and once with 100 ml of binding buffer, and then resuspended in 12.5 ml of binding buffer.
3. Preparation of SPAV5 binding reaction
To each assay well, the following were sequentially added into Optiplate plates:
 (i) Binding buffer to make up final volume of 125 µl per well.
 (ii) 3 µl (120 µg/well) of pretreated beads diluted with 22 µl of 50-OG Buffer
 (iii) 15 µg of $\alpha_v\beta_5$-cell lysate proteins.
 (iv) B-5 at 50,000 cpm.
 (v) 25 µl of graded concentrations of test compound.
 (vi) Each plate was sealed with plate sealer from PACKARD and incubated overnight with rocking at 4° C.
4. Plates were counted using PACKARD TOPCOUNT microplate scintillation counter.
5. % Inhibition was calculated as follows:
A=total counts (binding of receptor to B-5)
B=nonspecific counts (binding of receptor to B-5 in the presence of 2.5 µM cold ligand)
C=counts from receptor binding to test compound
% inhibition=$[\{(A-B)-(C-B)\}/(A-B)]/(A-B) \times 100$
$IC_{50}$ of test compound was calculated as 50% of inhibition.

Example of a Pharmaceutical Formulation

As a specific embodiment of an oral composition, 100 milligrams of a compound of the present invention are formulated with sufficient finely divided lactose to provide a total amount of 580 to 590 mg to fill a size 0 hard gel capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending

What is claimed is:

1. A compound of the structural formula I:

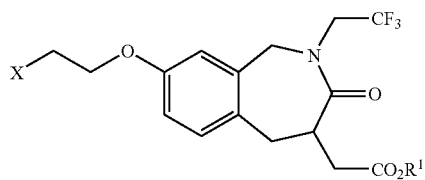

wherein X is selected from the group consisting of

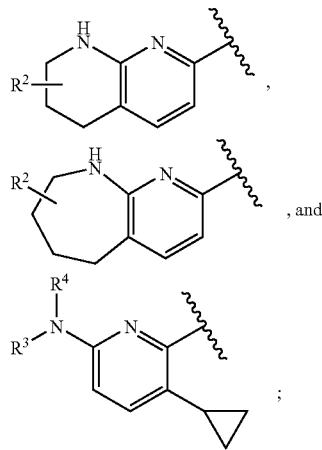

or a pharmaceutically acceptable salt thereof;
wherein the aromatic ring carbon atoms are unsubstituted or substituted with one $R^2$ substituent and the non-aromatic ring carbon atoms are unsubstituted or substituted with one or two $R^2$ substituents;
$R^2$ is selected from the group consisting of hydrogen, $C_{1-4}$ alkyl, and $C^{3-6}$ cycloalkyl; or two $R^2$ substituents, when on the same non-aromatic carbon atom, are taken together with the carbon atom to which they are attached to form a cyclopropyl group;
$R^1$ is hydrogen or $C_{1-4}$ alkyl; and
$R^3$ and $R^4$ are each independently hydrogen or $C^{1-4}$ alkyl.

2. The compound of claim 1 wherein $R^1$ is hydrogen.

3. The compound of claim 1 of structural formula II wherein the carbon atom marked with * has the (S) configuration:

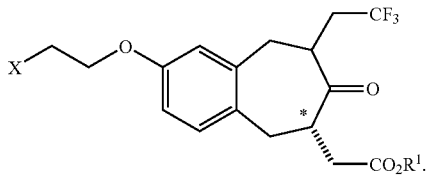

4. The compound of claim 3 which is

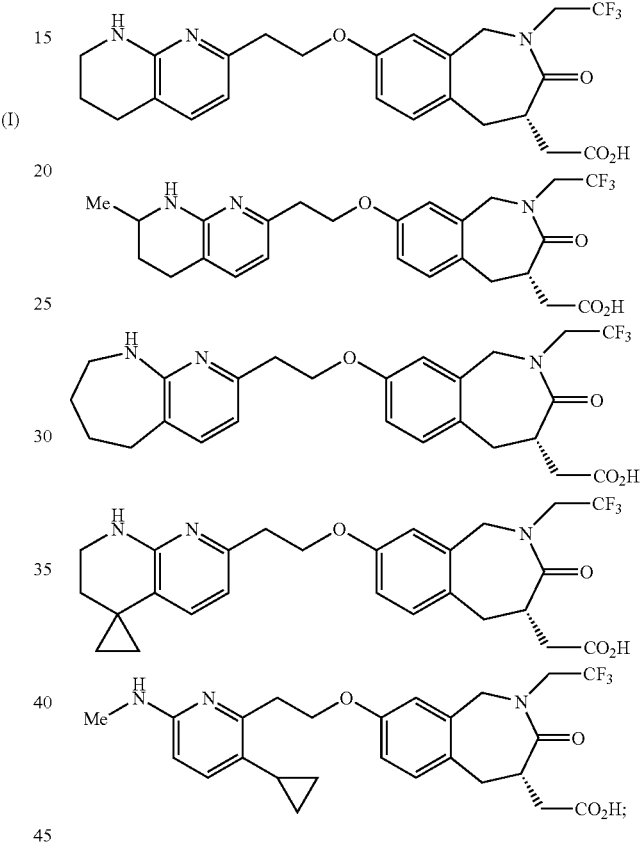

or a pharmaceutically acceptable salt thereof.

5. A pharmaceutical composition comprising a compound according to claim 1 and a pharmaceutically acceptable carrier.

6. A method of inhibiting a condition selected from the group consisting of bone resorption, restenosis, angiogenesis, diabetic retinopathy, macular degeneration, and inflammatory arthritis, comprising administering to a mammal in need thereof a therapeutically effective amount of a compound according to claim 1.

7. The method of claim 6 wherein the condition to be inhibited is bone resorption.

8. A method of inhibiting bone resorption in a mammal in need thereof, comprising administering to the mammal a therapeutically effective amount of the composition of claim 5.

9. A method of treating osteoporosis which comprises administering to a mammal in need of such treatment a therapeutically effective amount of a compound of claim 1.

* * * * *